United States Patent [19]

Hill et al.

[11] Patent Number: 4,945,172

[45] Date of Patent: Jul. 31, 1990

[54] PREPARATION OF N-FORMYL-L-ASPARTIC ANHYDRIDE

[75] Inventors: John B. Hill, Woodstock; Hugh L. Dryden, Jr., Deerfield; Robert Erickson, Des Plaines, all of Ill.

[73] Assignee: The Nutra Sweet Company, Deerfield, Ill.

[21] Appl. No.: 442,040

[22] Filed: Nov. 28, 1989

Related U.S. Application Data

[63] Continuation of Ser. No. 156,268, Feb. 12, 1988, abandoned.

[51] Int. Cl.$^5$ ............................................. C07D 307/22
[52] U.S. Cl. ..................................... 549/253; 562/898
[58] Field of Search ......................... 549/253; 562/898

[56] References Cited

U.S. PATENT DOCUMENTS

| | | | |
|---|---|---|---|
| 3,816,471 | 6/1974 | Ariyoshi et al. | 260/3468 |
| 4,526,985 | 7/1985 | Giobbio et al. | 549/253 |
| 4,550,180 | 10/1985 | Takemoto et al. | 549/253 |
| 4,810,816 | 3/1989 | Tsuji et al. | 560/41 |

*Primary Examiner*—Paul J. Killos
*Attorney, Agent, or Firm*—John M. Sanders; Jeffrey M. Hoster

[57] ABSTRACT

N-formyl-L-aspartic anhydride is prepared using a minimum excess of formic acid. Acetic anhydride and a $C_3$–$C_6$ secondary alcohol are added to the reaction mixture to consume excess formic acid. The reaction is suitable for further reactions without modification.

14 Claims, No Drawings

PREPARATION OF N-FORMYL-L-ASPARTIC ANHYDRIDE

This is a continuation of application Ser. No. 156,268, filed Feb. 12, 1988.

BACKGROUND OF THE INVENTION

The present invention relates to a method for the preparation of N-Formyl-L-Aspartic anhydride (F-Asp=O) which is used to prepare peptide sweeteners which contain a terminal aspartic acid moiety such as α-L-aspartyl-L-phenylalanine methyl ester (α-APM).

The aspartyl containing dipeptides are produced through a coupling reaction in which aspartic acid is joined with a second amino acid or derivatives thereof such as L-phenylalanine or its methyl ester. These coupling reactions require an amino protecting group attached to the aspartic acid moiety such as formyl, acetyl, acetoacetyl, benzyl, substituted and unsubstituted carbobenzoxy, t-butoxy carbonyl and the hydrohalide salt. The amino protecting group, often referred to in the art as the N-protecting group, for purposes of this disclosure shall be referred to as N-formyl since the formyl moiety functions as the blocking agent. Formylated aspartic anhydride is a widely used starting material and its process has been described extensively. See U.S. Pat. Nos. 4,173,562, 3,933,781 and 3,962,207 all of which are incorporated herein by reference.

Coupling reactions are carried out in a solvent and are common in several patented processes for the production of α-L-aspartyl-L-phenylalanine methyl ester (α-APM); see U.S. Pat. No. 3,962,207 to Uchiyama, U.S. Pat. No. 4,173,562 to Bachman and EPO Patent No. 127,411 to Yaichi et al., all of which are incorporated herein by reference.

N-Formyl-L-aspartic anhydride is usually produced from a reaction mixture of aspartic acid, a large excess of formic acid and acetic anhydride. The excess amount of formic acid must at some point be removed by distillation and separated from acetic acid which adds to the cost of the final product. The present invention avoids these extra distillation and separation procedures.

SUMMARY OF THE INVENTION

The present invention is directed to a process to prepare N-formyl-L-aspartic anhydride (F-Asp=O). The reaction by-products produced during formation of the F-Asp=O can serve as the solvent for a coupling reaction with another amino acid, such as, L-phenylalanine, in a manner that avoids many of the problems of separation and thereby reduces the cost of preparation.

F-Asp=O is prepared by reacting L-aspartic acid with formic acid in the presence of an effective amount of acetic anhydride under conditions sufficient to form N-formyl-L-aspartic anhydride. Then an effective amount of acetic anhydride and a $C_3$-$C_6$ secondary alcohol are added to the reaction mixture to consume excess formic acid. The resulting N-formyl-L-aspartic anhydride reaction mixture is suitable for further reactions without modifications.

Formyl-L-aspartic anhydride is usually prepared by combining aspartic acid with acetic anhydride and formic acid in reaction processes known in the art. See U.S. Pat. Nos. 3,933,781, 3,962,207 and 4,173,562. The present invention, however, utilizes a minimal amount of formic acid (1.2-1.35 Molar equivalents per mole of aspartic acid). Of particular interest, the excess formic acid is converted to isopropyl formate by the addition of acetic anhydride and isopropyl alcohol to the reaction mixture.

DESCRIPTION OF THE INVENTION

In practicing the present invention, L-aspartic acid is mixed with a minimal amount of formic acid (at least 1.2 Molar equivalents based on aspartic acid) and acetic anhydride (at least about 2.0 Molar equivalents based on aspartic acid) optionally in the presence of a catalyst, such as, magnesium oxide, resulting in the formation of N-formyl-L-aspartic anhydride.

Suitable catalysts include oxides, hydroxides and salts of metals and are disclosed in U.S. Pat. Nos. 4,508,912 and 4,550,180 which are incorporated herein by reference. This reaction is conducted at temperatures up to about 52° C. The mixture is preferably stirred at about 50° C. for at least about 2.5 hours. Additional acetic anhydride (about 0.2 moles) is added after about 2.5 hours in order to convert any excess, unreacted formic acid to formic-acetic anhydride, i.e., a mixed anhydride. After an additional 2.5 hours, a $C_3$-$C_6$ secondary alcohol, i.e., isopropyl alcohol (at least about 0.3 molar equivalents based on total formic acid added), is added to the reaction mixture to convert any formic-acetic anhydride to the corresponding ester, i.e., isopropyl formate. The amount of formic acid used is preferably 1.3 to 1.35 Molar equivalents based on aspartic acid.

Alternatively, the acetic anhydride can be added to the reaction mixture all at once (2.3-2.9 moles per mole of aspartic acid) at the beginning of the reaction and the secondary alcohol can be added thereafter to consume the excess formic acid by reacting with the mixed anhydride resulting in the formation of the corresponding ester. Also, a minor portion of the acetic anhydride can be added with the secondary alcohol in a single step. Preferably, however, the formic acid, a major amount of the acetic anhydride, and a catalyst are mixed for about 2-3 hours followed by addition of a minor portion of the acetic anhydride. The reaction is then maintained for an additional 2-3 hours with mixing after which the secondary alcohol (isoproponal) is added thereto. This final reaction mixture is then mixed, preferably at about 50° C., for an additional 2-3 hours to completion.

The product, N-formyl-L-aspartic anhydride, can then be reacted, i.e., coupled, with another amino acid such as L-phenylalanine or L-phenylalanine methyl ester in situ, thereby doing away with any costly and time-consuming separation techniques. The reaction by-products serve as cosolvents for the amino acid coupling reaction. The resulting dipeptides are intermediates in the preparation of aspartame.

The following examples are provided to specifically demonstrate the invention at hand. These examples are set forth by way of illustration only and it is intended that the invention is not to be construed as being limited either in spirit or in scope by the details contained herein as modifications in both. The materials and methods will be apparent from this disclosure to those skilled in the art.

EXAMPLE 1

0.12 grams (0.003 mole) of magnesium oxide, a catalyst, was dissolved in 16 milliliters (ml) (0.405 mole) of 95% formic acid. 60.2 ml of acetic anhydride was then added to the aforementioned solution which was heated to 35°-40° C. for 10-15 minutes. Subsequently, 39.93 grams (0.3 mole) of L-aspartic acid was added and this mixture was stirred for 2.5 hours at 50°±2° C. At this point, an additional 8.6 ml of acetic anhydride was added and the reaction continued for an additional 2.5 hours at 50°±2° C. 9.2 ml (0.120 mole) of isopropyl alcohol was then added to the reaction mixture and heating was continued for an additional two hours. N-formyl-L-aspartic anhydride was formed at this point as shown by high performance liquid chromatography (HPLC).

EXAMPLE 2

Magnesium oxide (0.121 grams; 0.003 mole) was dissolved in 16.4 ml (0.406 mole) of 93.4% formic acid under nitrogen. 62.5 ml (0.655 mole) of acetic anhydride was then added to the stirred mixture forming a white precipitate. The temperature of the mixture rose to 37°–38° C. during the course of the next thirty minutes. L-Aspartic acid (39.93 grams; 0.30 mole) was then added and the mixture heated to 48°–50° C. for 2.5 hours. Additional acetic anhydride (8.6 ml., 0.09 mole) was then added with heating for an additional 2.5 hours. 9.2 ml (0.120 mole) of isopropyl alcohol was added to the reaction mixture. Heating at 50°±2° C. was continued for an additional 2.0 hours. The reaction mixture was then cooled to room temperature (22°–27° C.).

EXAMPLE 3

Magnesium oxide (0.4 grams; 0.01 moles) was dissolved in 53.3 ml (1.35 moles) of 95% formic acid and 200 ml (2.10 moles) acetic anhydride. The reaction therein generated an increase in temperature to 40° C. (from 20°–22° C.) over a period of 15 minutes. L-aspartic acid (133.1 grams; 1.0 mole) was added to the reaction mixture and the resulting slurry was heated at 48°–50° C. for 2.5 hours at which point 28.9 ml (0.303 mole) of additional acetic anhydride was added. Heating was continued for another 2.5 hours after which 30.7 ml (0.4 mole) of isopropyl alcohol was mixed in. This mixture was stirred for 1.5 hours at 48°–50° C. and then permitted to cool to room temperature (25°±2° C.). The resulting mixture is suitable for further reactions without modification.

EXAMPLE 4

Formic acid (95.7%, 16 ml 0.405 mole) was added dropwise to 60.2 ml (0.631 mole) of acetic anhydride over 5 minutes during which time the temperature rose to 40° C. The mixture was stirred for 55 min and 0.43 g (0.003 moles) of magnesium acetate and 39.93 g (0.3 mole) of L-aspartic acid were added. The resulting slurry was heated at 47°–48° C. for 2.5 hr. Acetic anhydride (7.1 ml; 0.0744 mole) was added and the heating was continued for 2.5 hr. Isopropyl alcohol (7.21 g; 0.120 mole) was added and the heating was continued for 1.5 hr.

EXAMPLE 5

Formic acid (16.0 mls., 0.405 moles) was added to 0.121 g (0.003 mole) of magnesium oxide under nitrogen and stirred until all the solid was dissolved. Acetic anhydride (60.2 ml; 0.631 mole) was added, giving a precipitate immediately and a temperature increase to 40° C. over 15 min. L-aspartic acid (39.93 g; 0.3 mole) was added and the slurry heated to 48°–50° C. for 2.5 hr. Additional acetic anhydride (9.3 ml; 0.0974 mole) was added and heating continued for 2.5 hr isopropyl alcohol (11.9 ml; 0.155 mole) was added and the mixture heated for 1.5 hr.

In similar operations, various secondary alcohols and process conditions described herein are employed to produce N-formyl-L-aspartic anhydride wherein the final reaction mixture is suitable for further reactions without modification.

What is claimed is:
1. A method which comprises:
   (a) reacting L-aspartic acid with formic acid in the presence of an effective amount of acetic anhydride under conditions sufficient to form N-formyl-L-aspartic anhydride; and thereafter
   (b) adding to (a) above an effective amount of a $C_3$–$C_6$ secondary alcohol to consume excess formic acid wherein the resulting N-formyl-L-aspartic anhydride reaction mixture is suitable for further reactions without modification.
2. The method of claim 1 wherein the secondary alcohol is isopropanol and the reaction is conducted in the presence of a catalyst.
3. The method of claim 2 wherein (i) the formic acid is added to the reaction mixture in amounts of from about 1.25 to about 1.35 molar equivalents based on L-aspartic acid and (ii) the acetic anhydride is added in two stages, a major portion in step (a) and a minor portion in step (b).
4. The method of claim 3 wherein the acetic anhydride in step (a) is added in amounts of from about 2.1 to about 2.5 molar equivalents based on L-aspartic acid.
5. The method of claim 4 wherein the acetic anhydride in step (b) is added in an amount of from about 0.2 to about 0.4 molar equivalents based on L-aspartic acid.
6. The method of claim 5 wherein the isopropanol is added in an amount of from about 0.25 to about 0.5 molar equivalents bsased on L-aspartic acid.
7. The method of claim 6 wherein the reaction is conducted at a temperature under about 52° C.
8. The method of claim 7 wherein the temperature is about 50° C.
9. A method which comprises the sequential steps of:
   (a) reacting L-aspartic acid with formic acid in the presence of an effective amount of acetic anhydride under conditions sufficient to form N-formyl-L-aspartic anhydride;
   (b) adding a second portion of acetic anhydride to the reaction mixture; and thereafter
   (c) adding an effective amount of a $C_3$–$C_6$ secondary alcohol to consume excess formic acid,
wherein the resulting N-formyl-L-aspartic anhydride reaction mixture is suitable for further reactions without modification.
10. The method of claim 9 wherein the secondary alcohol is isopropanol and the reaction is conducted in the presence of a catalyst.
11. The method of claim 10 wherein
   (i) the formic acid is added to the reaction mixture in amounts of from about 1.25 to about 1.35 molar equivalents based on L-aspartic acid,
   (ii) the acetic anhydride in step (a) is added in amounts of from about 2.1 to about 2.5 molar equivalents based on L-aspartic acid, and
   (iii) the acetic anhydride in step (b) is added in amounts of from about 0.2 to about 0.4 molar equivalents based on L-aspartic acid.
12. The method of claim 11 wherein the isopropanol is added in an amount of from about 0.25 to about 0.5 molar equivalents based on L-aspartic acid.
13. The method of claim 12 wherein the reaction is conducted at a temperature under about 52° C.
14. The method of claim 13 wherein the temperature is about 50° C.

* * * * *